United States Patent [19]

Stahly et al.

[11] Patent Number: 4,499,026

[45] Date of Patent: Feb. 12, 1985

[54] NUCLEOPHILIC SUBSTITUTION PROCESS

[75] Inventors: Barbara C. Stahly; G. Patrick Stahly, both of Baton Rouge, La.

[73] Assignee: Ethyl Corporation, Richmond, Va.

[21] Appl. No.: 452,618

[22] Filed: Dec. 23, 1982

Related U.S. Application Data

[63] Continuation-in-part of Ser. No. 411,554, Aug. 25, 1982, abandoned.

[51] Int. Cl.$^3$ ............................................. C07C 121/50
[52] U.S. Cl. ................................................ 260/465 R
[58] Field of Search ................................... 260/465 R

[56] References Cited

PUBLICATIONS

Golinki et al., Tetrahedron Letter, No. 37, pp. 3495–3498, (1978).

Makosza et al., J. Org. Chem., vol. 45, pp. 1534–1535, (1980).

Mabosza, Int. Conf. Chem. Biotechol. Biol. Act. Nat. Prod. (Proc.), vol. 2, pp. 480–490, (1981).

Primary Examiner—Delbert R. Phillips
Attorney, Agent, or Firm—Donald L. Johnson; John F. Sieberth; Patricia J. Hogan

[57] ABSTRACT

Nitroarylacetonitriles are prepared by reacting a nitroaromatic compound which is devoid of halogen on the aromatic ring carrying a nitro group with an alpha,alpha-disubstituted acetonitrile in an inert solvent and in the presence of a base so that the nitrile undergoes a nucleophilic substitution on an unsubstituted ring carbon of the nitroaromatic compound during which an alpha-substituent functions as a leaving group. Nitrobenzene acetic acids and their nitriles are useful intermediates for the synthesis of pharmaceuticals.

19 Claims, No Drawings

NUCLEOPHILIC SUBSTITUTION PROCESS

CROSS-REFERENCE

This application is a continuation-in-part of copending application Ser. No. 411,554, filed Aug. 25, 1982, now abandoned.

TECHNICAL FIELD

This invention relates to nitroarylacetonitriles and derivatives thereof—more particularly to processes for preparing the nitriles and derivatives.

BACKGROUND

It is known that nitrobenzene acetic acids and their nitriles are particularly useful intermediates for the synthesis of pharmaceuticals. For example, 2-[4-(1,3-dihydro-1-oxo-2H-isoindol-2-yl)phenyl]propionic acid—an anti-inflammatory and analgesic agent commonly known as indoprofen—can be prepared from a 2-(4-nitrobenzene)propionic acid intermediate by hydrogenating the intermediate, reacting the resultant 2-(4-aminobenzene)propionic acid with phthalic anhydride, and reducing the resultant 2-(4-phthalimidophenyl)propionic acid, e.g., with zinc and formic acid. Also, 2-[4-(1,3-dihydro-1-oxo-2H-isoindol2-yl)phenyl]butyric acid—commonly known as indobufen—can be formed in a similar manner from 2-(4-nitrobenzene)butyric acid.

In the past, a disadvantage of employing nitrobenzene acetic acids or nitriles as pharmaceutical intermediates has been the difficulty of preparing those intermediates by conventional techniques. For example, 2-(4-nitrobenzene)propionic acid has been customarily formed by a three-step procedure wherein (1) 4-ethylnitrobenzene is reacted with sodium phenoxide and carbon dioxide to produce disodium 2-methyl-2-(4-nitrobenzene)malonate, (2) the malonate salt is converted by acidification into the corresponding diacid, and (3) the diacid is heated to effect decarboxylation.

It would obviously be a welcome contribution to the art to provide a method of synthesizing nitrobenzeneacetonitriles and analogs and derivatives thereof in a simple, straightforward manner.

STATEMENT OF INVENTION

An object of this invention is to provide novel processes for preparing nitroarylacetonitriles.

Another object is to provide such processes which permit the preparation of the nitriles in moderate-to-good yield with high selectivity in a very simple and straightforward manner.

A further object is to provide novel, improved processes for preparing derivatives of nitroarylacetonitriles.

These and other objects are attained by (A) reacting a nitroaromatic compound which is devoid of halogen on the aromatic ring carrying a nitro group with an alpha,alpha-disubstituted acetonitrile in an inert solvent and in the presence of a base so that the nitrile undergoes a nucleophilic substitution on an unsubstituted ring carbon of the nitroaromatic compound during which an alpha-substituent functions as a leaving group, thereby forming a nitroarylacetonitrile, and (B) when appropriate, converting the nitroarylacetonitrile to a desired derivative thereof.

DETAILED DESCRIPTION

Nitroaromatic compounds utilizable in the practice of the invention include a variety of such compounds—the chief requirements for their utility being that (1) they bear at least one nitro substituent on an aromatic ring, (2) they contain at least one replaceable hydrogen on an aromatic ring to which a nitro group is attached, and (3) they be devoid of substituents which would interfere with the desired nucleophilic substitution reaction.

Thus, the utilizable nitroaromatic compounds include compounds having one or more simple or fused aromatic rings containing five or six members and either bearing no substituents other than nitro substituents or also bearing any of a variety of inert substituents, i.e., substituents that do not interfere with the desired nucleophilic substitution reaction, such as alkyl, alkoxy, alkylmercapto, trifluoromethyl, dialkylamino, dialkanoylamino, cyano, dialkylcarbamoyl, alkylsulfonyl, dialkylsulfamoyl, alkoxyalkyl, haloalkyl, cycloalkyl, halocycloalkyl, etc.—any alkyl chains in the substituents generally being lower alkyl, i.e., $C_1$–$C_6$ alkyl, chains. When the nitroaromatic compound contains more than one ring, any such inert substituent may be on the same ring as the ring bearing a nitro substituent and/or on a ring which is directly or indirectly attached to the ring bearing a nitro substituent, and any such inert substituent may be a halo substituent if it is on a ring other than a ring carrying a nitro group.

When the aromatic ring bearing the required nitro substituent is a six-membered ring, there will be at least one replaceable hydrogen in a position para or ortho to the carbon bearing the nitro substituent; and it is preferred that there be a replaceable hydrogen in the para position. Nitroaromatic compounds having a five-membered ring should have a replaceable hydrogen on a carbon adjacent to, or separated by two ring atoms from, the carbon bearing the nitro substituent.

Illustrative of nitroaromatic compounds that may be used in the practice of the invention are heterocyclic compounds which preferably contain five or six-membered rings having aromatic character, such as nitropyridine-N-oxide, 5-nitroisoquinoline, 5- and 6-nitroquinolines, 2-nitrothiophene, etc.; fused-ring aromatic compounds, such as the 1- and 2-nitronaphthalenes, etc.; aromatic compounds containing a plurality of simple rings, such as the 2-, 3-, and 4-nitrophenyls, the 2-, 3-, and 4-benzylnitrobenzenes, 2-nitrodiphenyl ether, etc.; and aromatic compounds containing a single simple ring, such as nitrobenzene, 2-methylnitrobenzene, the 2,3-, 2,5-, and 3,5-dimethylnitrobenzenes, the 2,4- and 2,6-diethylnitrobenzenes, 3,4-dibutylnitrobenzene, the 1,2- and 1,3-dinitrobenzenes, 2,6-dinitrotoluene, the 1,2,3- and 1,2,4-trinitrobenzenes, 2-nitro-N,N-diethylaniline, 4-nitro-N-ethylacetanilide, 2-nitrobenzylcyanide, 2-nitrophenyl acetate, etc.

In some cases, polynitroaromatic reactants may undergo substitution reactions whereby one of the nitro groups is replaced by the nitrile reactant. Therefore, the possibility of this competitive reaction should be kept in mind when selecting a polynitroaromatic for use in the process.

The preferred nitroaromatic compounds are nitrobenzenes having a replaceable hydrogen in the position para to the nitro group, since the nucleophilic substitution reaction of the invention tends to be highly selective on the para position, and the use of such compounds therefore leads to the production of nitrobenzeneacetonitriles which are ideally suited for the synthesis of anti-inflammatory agents of the type mentioned above. Particularly preferred is nitrobenzene, which is readily converted with high selectivity into pharmaceutically-active agents such as 2-[4-(1,3-dihydro-1-oxo-2H-isoindol-2-yl)phenyl]propionic acid, 2-[4-(1,3-dihydro-1-oxo-2H-isoindol-2-yl)phenyl]butyric acid, and analogs thereof.

The alpha,alpha-disubstituted acetonitriles that can be used in the practice of the invention also include a variety of such compounds, which—in general—may be represented by the formula:

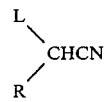

wherein L is a leaving group and R is halo (preferably chloro) or, more preferably, a hydrocarbyl (e.g., alkyl, alkenyl, alkynyl, cycloalkyl, cycloalkenyl, aryl, aralkyl, etc.) or hydrocarbyloxyhydrocarbyl (e.g., alkoxyalkyl, aryloxyalkyl, alkoxyaryl, alkoxycycloalkyl, etc.) group which most preferably contains up to about 10 carbons.

Exemplary leaving groups, L, include halo, aryloxy, haloaryloxy, alkylthio, cycloalkylthio, arylthio, aralkylthio, haloalkylthio, halocycloalkylthio, haloarylthio, haloaralkylthio, or, less preferably, alkoxy, cycloalkoxy, aralkoxy, haloalkoxy, halocycloalkoxy, haloaralkoxy, and the like, as well as other suitable leaving groups which have been described in the literature, e.g., in Golinski et al., "'Vicarious' Nucleophilic Substitution of Hydrogen in Aromatic Nitro Compounds, *Tetrahedron Letters*, Vol. 37, pp. 3495-8 (1978) and in Makosza et al., "Vicarious Substitution of Hydrogen in Aromatic Nitro Compounds with Acetonitrile Derivatives," *Journal of Organic Chemistry*, Vol. 45, pp. 1534-5 (1980).

When the leaving group is an organic group, it is generally preferred that it contain not more than about 10 carbons, although organic leaving groups having an even higher carbon content are satisfactory in the practice of the invention. Preferably, the leaving group is halo, i.e., chloro, bromo, fluoro, or iodo; and it is more preferably chloro or bromo, most preferably chloro.

A few examples of alpha,alpha-disubstituted acetonitriles that can be used in the practice of the invention are 2-chloropropionitrile, 2-chlorobutyronitrile, 2-chlorovaleronitrile, 2-chlorocapronitrile, 2-chloro-4-pentenenitrile, 2-chloro-3,3-dimethylbutyronitrile, 2-chloro-2-phenylacetonitrile, 2-chloro-2-cyclohexylacetonitrile, 2-chloro-3-(3-chloro-o-tolyl)propionitrile, 2-chloro-3-phenylpropionitrile, the corresponding bromo and iodo compounds, and the like. The alpha-halo-alpha-hydrocarbylacetonitriles, i.e., alpha-haloalkyl cyanides containing at least three carbons—particularly 2-chloropropionitrile and 2-bromopropionitrile—are especially preferred, although similar cyanides in which the alpha-halo substituent is replaced by one of the other leaving groups mentioned above are also highly desirable.

In another highly desirable embodiment of the invention, the alpha,alpha-disubstituted acetonitrile is an alpha,alpha-dihaloacetonitrile, most preferably an alpha,alpha-dichloroacetonitrile, which leads to the formation of a product having a reactive halo substituent in the alpha-position, e.g., a product corresponding to the formula:

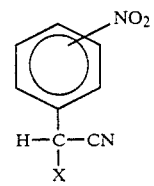

wherein x is halo, preferably chloro. Such products enable facile synthesis of a variety of end products. Most preferably the nitro group is in the position para to the nitrile substituent, although it may be located in an ortho position.

It is noted that attempts to employ 2-chloroacetonitrile in the process of the invention have been unsuccessful thus far. No reaction was detected when an attempt was made to react nitrobenzene with 2-chloroacetonitrile in the presence of sodium hydride in N,N-dimethylformamide. In this connection, it is interesting to note the results reported in the aforementioned Makosza et al. article, viz., the success in reacting chloroacetonitrile with 1-nitronaphthalene and 4-chloronitrobenzene in the presence of sodium hydroxide in dimethylsulfoxide to form the corresponding alpha-nitroarylacetonitriles vs. the lack of success in effecting a substitution process when nitrobenzene was the nitroaromatic compound employed.

The solvent used in a nucleophilic substitution process of the invention may be any solvent that is inert under the conditions of the reaction, i.e., any solvent that will not prevent the reaction from occurring. Such solvents are substantially anhydrous and are generally aprotic, although solvents such as liquid ammonia are also utilizable.

Illustrative aprotic solvents which may be employed in the process of the invention include ethers such as diethyl ether, dibutyl ether, 1-ethoxyhexane, tetrahydrofuran, 1,4-dioxane, 1,3-dioxolane, diglyme, 1,2-diethoxyethane, anisole, etc.; tertiary amines such as pyridine, N-ethylpiperidine, triethyl amine, tributyl amine, N,N-diphenyl-N-methyl amine, N,N-dimethylaniline, etc.; and other aprotic solvents. However, the preferred aprotic solvents are dipolar aprotic solvents such as dimethyl sulfoxide, N,N-dimethylformamide, N,N-dimethylacetamide, dimethyl sulfone, tetramethylene sulfone, N-methylpyrrolidinone, and the like.

Bases useful in the practice of the invention include all bases strong enough to activate the nitrile reactant, e.g., alkaline earth metal compounds such as calcium oxide, calcium hydride, calcium hydroxide, barium oxide, barium hydroxide, magnesium hydroxide, zinc hydroxide, etc. However, the base is preferably an alkali metal compound, e.g., an organoalkali metal compound, alkali metal hydride, alkali metal hydroxide, alkali metal oxide, alkali metal amide, or alkali metal alcoholate, such as butyllithium, phenyllithium, ethylsodium, amylsodium, butylpotassium, benzylpotassium, sodium dimsylate (i.e., the sodium salt of diethylsulfoxide), sodium hydride, potassium hydride, sodium hydroxide, potassium hydroxide, sodium oxide, potassium oxide, sodium amide, potassium amide, lithium diisopropylamide, sodium methoxide, potassium t-butoxide, the sodium salt of the monomethylether of ethylene glycol, sodium phenoxide, and the like. Ordinarily the use of sodium hydride, potassium hydride, or potassium t-butoxide will be found most convenient and economical.

Use of an alkali metal compound as the base permits the alternatives of using the alkali metal compound alone or in conjunction with a phase transfer catalyst, such as a quaternary ammonium salt, ethylene glycol, or a suitable crown ether. When a phase transfer catalyst is employed (1) the alkali metal compound may be any of the alkali metal compounds generically or specifically indicated above, although the type of alkali metal compound being used determines the type of crown ether that is preferably utilized—lithium bases generally calling for the use of a 12-crown-4 ether, sodium bases generally calling for the use of a 15-crown-5 ether, and potassium bases generally calling for the use of an 18-crown-6 ether, and (2) the reaction medium may be any of the aprotic solvents mentioned above, or it may be an inert liquid hydrocarbon such as benzene, toluene, xylene, hexane, heptane, isooctane, or the like.

When an alkali metal hydride, especially a highly pure alkali metal hydride, is employed as the base, it is desirable to include a small amount of a transfer agent such as water, alcohol, or the like in the system. It is believed that the transfer agent activates the hydride by reacting therewith to form a small amount of the alkali metal hydroxide or alcoholate.

The nitroarylacetonitrile synthesis of the invention is conducted in a substantially anhydrous reaction system, and accordingly, except when a small amount of water (which is itself consumed by reaction with the alkali metal hydride) is employed as a transfer agent, the components of the reaction system should be brought together and maintained under a dry inert atmosphere. Thus, while it is possible to conduct the process in the presence of air, it is desirable to maintain the reaction system under an atmosphere of dry nitrogen or the like. Since the reaction itself is normally an exothermic reaction, with its initiation readily ascertainable by noting the exotherm produced, the reactants are ordinarily brought together at ambient temperatures, although the temperature may be raised or lowered to suit the needs of the occasion if desired.

The nitroaromatic compound and alpha,alpha-disubstituted acetonitrile may be used in amounts such as to provide a stoichiometric excess of either of the reactants or the stoichiometric amount of each. However, when a stoichiometric excess of the nitroaromatic compound is employed, the quantity of product obtainable will be limited by the quantity of nitrile used, so it is desirable to utilize a stoichiometric excess of the nitrile. The amount of base employed is preferably such as to provide at least two molar equivalents of base per mol of nitroaromatic compound, since the use of smaller amounts—although permitting the reaction to occur—makes the base the limiting reagent.

The mode of addition of the ingredients of the reaction system is not particularly critical. Accordingly, it is convenient to add the nitroaromatic compound to a mixture of the other materials, add the base to a mixture of the other materials, add the reactants to a mixture of the base and inert solvent, introduce all four ingredients simultaneously into the reaction zone, or the like. Since the reaction ordinarily proceeds very rapidly, long reaction times are not required. The reaction will usually be completed within a matter of minutes or a few hours at ambient temperatures.

When derivatives of the nitroarylacetonitriles are desired, they may be prepared by employing conventional techniques to convert to the desired derivatives the nitroarylacetonitriles made in accordance with the present invention. Thus, for example:

(A) 2-(4-nitrobenzene)propionitrile synthesized by the process of the invention may be hydrolyzed to 2-(4-nitrobenzene)propionic acid, which in turn may be hydrogenated to 2-(4-aminobenzene)propionic acid, reacted with phthalic anhydride to form 2-(4-phthalimidophenyl)propionic acid, and reduced to indoprofen, (B) 2-(4-nitrobenzene)propionitrile synthesized by the process of the invention may be hydrogenated to 2-(4-aminobenzene)propionitrile, hydrolyzed to 2-(4-aminobenzene)propionic acid, reacted with phthalic anhydride to form 2-(4-phthalimidophenyl)propionic acid, and reduced to indoprofen, (C) 2-(4-nitrobenzene)propionitrile synthesized by the process of the invention may be hydrogenated to 2-(4-aminobenzene)propionitrile, reacted with phthalic anhydride to form 2-(4-phthalimidophenyl)propionitrile, and hydrolyzed and reduced (in either order) to indoprofen, and (D) 2-(4-nitrobenzene)butyronitrile synthesized by the process of the invention may be subjected to the same reactions to prepare indobufen or indobufen intermediates.

The particular conventional techniques used to convert the nitroarylacetonitriles into their various derivatives are not critical. It may sometimes be desirable to use certain particular techniques for the preparation of the derivatives, e.g., the techniques taught in Section No. 8(c), pages 2–11, of Adria Laboratories' NDA on Indoprofen Capsules, on file with the Federal Drug Administration, the disclosures of which are incorporated herein by reference. However, the overall processes for preparing the derivatives are simplified and made more efficient and economical by the present simplification of the synthesis of the nitroarylacetonitriles, regardless of the particular techniques used to convert them into their various derivatives.

As indicated above, the present invention is particularly advantageous in providing a readier and more economical route to the synthesis of pharmaceuticals and other chemical products that can be prepared from nitroarylacetonitriles. Such products include, not only those mentioned above, but a variety of products, such as products disclosed in U.S. Pat. Nos. 3,641,040, 3,657,230, 3,767,805, 3,868,391, 3,936,467, 3,993,763, 3,997,669, 4,010,274, 4,118,504, 4,126,691, 4,163,788, and 4,239,901.

The following examples are given to illustrate the invention and are not intended as a limitation thereof.

EXAMPLE I

Into a flask under nitrogen were placed 4.0 g of 60% sodium hydride in mineral oil (0.10 mole). The sodium hydride was washed with three 10 ml portions of petroleum ether (b.p. 35°–60° C.) and was slurried in 50 ml of N,N-dimethylformamide (DMF). A solution of 12.3 g of nitrobenzene (0.10 mole) and 9.0 g of 2-chloropropionitrile (0.10 mole) in 10 ml of DMF was added dropwise to the slurry. An ice water bath was applied to the mixture periodically so that the temperature did not exceed 45° C. After the addition was complete (30 minutes) the purple mixture was allowed to react for 30 minutes and was poured into 200 ml of cold 10% HCl. The aqueous mixture was extracted with three 100 ml portions of diethyl ether, and the ether layers were combined, dried over magnesium sulfate, and concentrated to give a dark oil. Excess nitrobenzene and DMF were removed from this oil at 50° C. (at 1 mm pressure) and the residue was chromatographed on a column of 400 g of silica gel which was eluted with dichloromethane. A fraction was collected containing 2.9 g of 2-(4-nitrobenzene)propionitrile (16.5% yield).

EXAMPLE II

Into a flame dried flask under nitrogen were placed 500 mg of 60% sodium hydride in mineral oil (12.5 mmole). The sodium hydride was washed with three 5 ml portions of petroleum ether (b.p. 35°–60° C.) and was slurried in 4 ml of N,N-dimethylformamide (DMF). One drop of a solution of 770 mg of nitrobenzene (6.25 mmole) and 600 mg of a 2-chloropropionitrile (6.70 mmole) in 1 ml of DMF was added to the sodium hydride slurry to give a deep purple solution. After one minute the mixture was placed in an ice water bath and the rest of the reactant solution was added dropwise. The resulting mixture was stirred at 0° C. for 15 minutes and was poured into 50 ml of 1N HCl. The aqueous mixture was extracted with three 40 ml portions of diethyl ether, and the ether layers were combined, dried (MgSO₄), and concentrated to give 880 mg of black oil. Purification of 208 mg of this oil on one 2 mm silica gel plate eluted with 50% dichloromethane/50% petroleum ether afforded 51.2 mg (20% yield) of 2-(4-nitrobenzene)propionitrile.

EXAMPLE III

Into a flame dried flask under nitrogen were placed 176 mg of potassium t-butoxide (1.57 mmoles), 23 mg of dibenzo 18-crown-6 (0.064 mmole), and 1.0 ml of toluene. While this mixture was vigorously stirred in a room temperature water bath, a solution of 106 mg of 1,3-dinitrobenzene (0.631 mmole) and 71 mg of 2-chloropropionitrile (0.79 mmole) in 0.5 ml of toluene was added dropwise. The resulting purple mixture was stirred for 15 minutes and poured into 20 ml of 1N HCl. The aqueous mixture was extracted with three 20 ml portions of diethyl ether, and the ether layers were combined, dried (MgSO₄), concentrated, and placed on one 2 mm silica gel TLC plate. One development with 50% petroleum ether (35°–60° C.)/50% dichloromethane afforded 10 mg of 1,3-dinitrobenzene (9% recovery) and 25 mg of 2-(2,4-di-nitrobenzene)propionitrile (18% yield).

As noted above, a feature of this invention is the fact that the nitrile is an acetonitrile having two alpha-substituents. The following Comparative Example serves to illustrate this requirement.

COMPARATIVE EXAMPLE

Into a flame dried flask under nitrogen were placed 500 mg of 60% sodium hydride in mineral oil (12.5 mmole). The sodium hydride was washed with three 5 ml portions of petroleum ether b.p. 35°–60° C.), slurried in 4 ml of N,N-dimethylformamide (DMF), and cooled in an ice water bath. A solution of 770 mg of nitrobenzene (6.25 mmole) and 500 mg of chloroacetonitrile (6.62 mmole) in 1 ml of DMF was added dropwise. The resulting brown mixture was stirred at 0° C. for 15 minutes and was poured into 50 ml of 1N HCl. The aqueous mixture was extracted with three 40 ml portions of diethyl ether, and the ether layers were combined, dried (MgSO₄), and concentrated to give 1.02 g of black oil. Thin layer chromatographic analysis of this oil revealed no substitution product; only nitrobenzene and an immobile brown spot were observed.

We claim:

1. A process which comprises reacting a nitrobenzene which is devoid of halogen on the aromatic ring with an alpha-haloacetonitrile corresponding to the formula:

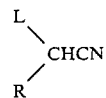

wherein L is halo and R is an alkyl group containing 1–10 carbons in an inert substantially anhydrous dipolar aprotic solvent and in the presence of a strong alkali metal compound base so that the nitrile undergoes a nucleophilic substitution on an unsubstituted ring carbon of the nitrobenzene during which the alpha-halo substituent functions as a leaving group, thereby forming a 2-(nitrobenzene)acetonitrile.

2. The process of claim 1 wherein the nitroaromatic compound is a mononitrobenzene.

3. The process of claim 2 wherein the mononitrobenzene is nitrobenzene.

4. The process of claim 1 wherein the nitroaromatic compound is a dinitrobenzene.

5. The process of claim 1 wherein the alpha-halo substituent is chloro or bromo.

6. The process of claim 1 wherein the alpha-haloacetonitrile is 2-chloropropionitrile.

7. The process of claim 1 wherein the base is an alkali metal hydride.

8. The process of claim 7 wherein the alkali metal hydride is sodium hydride or potassium hydride.

9. The process of claim 1 wherein the base is potassium t-butoxide.

10. The process of claim 1 wherein the solvent is N,N-dimethylformamide and the base is sodium hydride or potassium hydride.

11. The process of claim 1 wherein a mononitrobenzene having an unsubstituted position para to the nitro group is reacted with the alpha-haloacetonitrile so as to form a 2-(4-nitrobenzene)acetonitrile.

12. The process of claim 11 wherein the alpha-haloacetonitrile is an alpha-chloro- or alpha-bromoacetonitrile.

13. A process which comprises reacting nitrobenzene with 2-chloro-, 2-bromo-, or 2-iodopropionitrile in a substantially anhydrous dipolar aprotic solvent and in the presence of a strong alkali metal compound base so that the nitrile undergoes a nucleophilic substitution on an unsubstituted ring carbon of the nitrobenzene during which the alpha-halo substituent functions as a leaving group, thereby forming 2-(4-nitrobenzene)propionitrile.

14. The process of claim 13 wherein (A) the nitrobenzene is reacted with the 2-halopropionitrile to form 2-(4-nitrobenzene)propionitrile and (B) the 2-(4-nitrobenzene)propionitrile is converted to 2-(4-aminobenzene)propionic acid by:

(1) hydrolyzing the 2-(4-nitrobenzene)propionitrile to 2-(4-nitrobenzene)propionic acid and hydrogenating the 2-(4-nitrobenzene)propionic acid to 2-(4-aminobenzene)propionic acid or (2) hydrogenating the 2-(4-nitrobenzene)propionitrile to 2-(4-aminobenzene)propionitrile and hydrolyzing the 2-(4-aminobenzene)propionitrile to 2-(4-aminobenzene)propionic acid.

15. The process of claim 14 wherein (A) the nitrobenzene is reacted with the 2-halopropionitrile to form 2-(4-nitrobenzene)propionitrile, (B) the 2-(4-nitrobenzene)propionitrile is converted to (2-(4-aminobenzene)-propionic acid, and (C) the 2-(4-aminobenzene)propionic acid is reacted with phthalic anhydride to form 2-(4-phthalimidophenyl)propionic acid.

16. The process of claim 15 wherein (A) the nitrobenzene is reacted with the 2-halopropionitrile to form 2-(4-nitrobenzene)propionitrile, (B) the 2-(4-nitrobenzene)propionitrile is converted to 2-(4-aminobenzene)-propionic acid, (C) the 2-(4-aminobenzene)propionic acid is reacted with phthalic anhydride to form 2-(4-phthalimidophenyl)propionic acid, and (D) the 2-(4-phthalimidophenyl)propionic acid is reduced to indoprofen.

17. The process of claim 13 wherein (A) the nitrobenzene is reacted with the 2-halopropionitrile to form 2-(4-nitrobenzene)propionitrile and (B) the 2-(4-nitrobenzene)propionitrile is hydrogenated to 2-(4-aminobenzene)propionitrile.

18. The process of claim 17 wherein (A) the nitrobenzene is reacted with the 2-halopropionitrile to form 2-(4-nitrobenzene)propionitrile, (B) the 2-(4-nitrobenzene)propionitrile is hydrogenated to 2-(4-aminobenzene)propionitrile, and (C) the 2-(4-aminobenzene)propionitrile is reacted with phthalic anhydride to form 2-(4-phthalimidophenyl)propionitrile.

19. The process of claim 18 wherein (A) the nitrobenzene is reacted with the 2-halopropionitrile to form 2-(4-nitrobenzene)propionitrile, (B) the 2-(4-nitrobenzene)propionitrile is hydrogenated to 2-(4-aminobenzene)propionitrile, (C) the 2-(4-aminobenzene)propionitrile is reacted with phthalic anhydride to form 2-(4-phthalimidophenyl)propionitrile, and (D) the 2-(4-phthalimidophenyl)propionitrile is converted to indoprofen by:

(1) hydrolyzing the 2-(4-phthalimidophenyl)propionitrile to 2-(4-phthalimidophenyl)propionic acid and reducing that acid to indoprofen or (2) reducing the 2-(4-phthalimidophenyl)propionitrile to 2-[4-(1,3-dihydro-1-oxo-2H-isoindol-2-yl)phenyl]propionitrile and hydrolyzing the resulting nitrile to indoprofen.

* * * * *